(12) United States Patent
Anderson

(10) Patent No.: US 11,401,364 B2
(45) Date of Patent: *Aug. 2, 2022

(54) BISPHENOL M DIPHTHALONITRILE ETHER RESIN, BISPHENOL P DIPHTHALONITRILE ETHER RESIN, METHODS OF MAKING SAME, RESIN BLENDS, AND TWO COMPONENT SYSTEMS

(71) Applicant: 3M INNOVATIVE PROPERTIES COMPANY, St. Paul, MN (US)

(72) Inventor: Benjamin J. Anderson, Eden Prairie, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 976 days.

This patent is subject to a terminal disclaimer.

(21) Appl. No.: 16/078,073

(22) PCT Filed: Mar. 24, 2017

(86) PCT No.: PCT/US2017/024006
§ 371 (c)(1),
(2) Date: Aug. 21, 2018

(87) PCT Pub. No.: WO2017/172515
PCT Pub. Date: Oct. 5, 2017

(65) Prior Publication Data
US 2019/0047946 A1    Feb. 14, 2019

Related U.S. Application Data

(60) Provisional application No. 62/475,396, filed on Mar. 23, 2017, provisional application No. 62/348,477,
(Continued)

(51) Int. Cl.
*C08G 16/02* (2006.01)
*C08G 73/00* (2006.01)
(Continued)

(52) U.S. Cl.
CPC ........ *C08G 16/0231* (2013.01); *C07C 255/54* (2013.01); *C07C 323/32* (2013.01);
(Continued)

(58) Field of Classification Search
None
See application file for complete search history.

(56) References Cited

U.S. PATENT DOCUMENTS 3,429,722 A    2/1969   Economy
3,496,250 A    2/1970   Czerwinski
(Continued)

FOREIGN PATENT DOCUMENTS

CN    101395201    3/2009
CN    101831173    9/2010
(Continued)

OTHER PUBLICATIONS

Canlica, "Synthesis, characterization and electrochemical, and electrical measurements of novel 4,4'-1isopropylidendioxydiphenyl bridged bis and cofacial bis-metallophthalocyanines (Zn.Co)," Polyhedron, 2008, vol. 27, No. 7, pp. 1883-1890, XP022627496.
(Continued)

*Primary Examiner* — Megan McCulley
(74) *Attorney, Agent, or Firm* — Adrian L. Pishko

(57) ABSTRACT

Resins are provided including bisphenol M diphthalonitrile ether resin or bisphenol P diphthalonitrile either resin. Compositions are also provided, including a primary amine curative and the bisphenol M diphthalonitrile ether resin or the bisphenol P diphthalonitrile either resin. Further, polymerized products are provided of the bisphenol M diphtha-
(Continued)

lonitrile ether resin or the bisphenol P diphthalonitrile either resin. In addition, a method of making a polymerized network is provided. A two component system is further provided, including a curative in one of the components and the bisphenol M diphthalonitrile ether resin or the bisphenol P diphthalonitrile either resin in the other component. In addition, a resin blend is provided, including a blend of at least two of bisphenol M diphthalonitrile ether resin, bisphenol P diphthalonitrile either resin, or bisphenol T diphthalonitrile ether resin.

12 Claims, 1 Drawing Sheet

Related U.S. Application Data filed on Jun. 10, 2016, provisional application No. 62/316,248, filed on Mar. 31, 2016.

(51) Int. Cl.
*C08L 71/00* (2006.01)
*C07C 255/54* (2006.01)
*C07C 323/32* (2006.01)
*C08L 61/00* (2006.01)

(52) U.S. Cl.
CPC .............. *C08G 73/00* (2013.01); *C08L 61/00* (2013.01); *C08L 71/00* (2013.01); *C08L 2205/025* (2013.01); *C08L 2205/035* (2013.01)

(56) References Cited

U.S. PATENT DOCUMENTS

| | | | |
|---|---|---|---|
| 3,956,320 | A | 5/1976 | Heath |
| 4,223,123 | A | 9/1980 | Keller |
| 4,304,896 | A | 12/1981 | Keller |
| 4,408,035 | A | 10/1983 | Keller |
| 4,587,325 | A | 5/1986 | Keller |
| 4,764,578 | A | 8/1988 | Malinge |
| 5,003,039 | A | 3/1991 | Keller |
| 5,262,514 | A | 11/1993 | Keller |
| 5,312,887 | A | 5/1994 | Papathomas |
| 5,780,154 | A | 7/1998 | Okano |
| 6,001,926 | A | 12/1999 | Sastri |
| 6,297,298 | B1 | 10/2001 | Keller |
| 7,049,353 | B2 | 5/2006 | Conroy |
| 8,921,510 | B1 | 12/2014 | Keller |
| 9,221,970 | B2 | 12/2015 | Schultz |
| 10,556,859 | B2 | 2/2020 | Lee |
| 2012/0214948 | A1 | 8/2012 | Condo |
| 2012/0245253 | A1 | 9/2012 | Schultz |
| 2014/0275472 | A1 | 9/2014 | Keller |
| 2018/0265456 | A1* | 9/2018 | Fuchs ..................... A61P 35/00 |

FOREIGN PATENT DOCUMENTS

| | | |
|---|---|---|
| CN | 102086168 | 6/2011 |
| CN | 102887999 | 1/2013 |
| CN | 102936340 | 2/2013 |
| CN | 102936466 | 2/2013 |
| CN | 103012790 | 4/2013 |
| CN | 105348734 | 2/2016 |
| JP | 62-149723 | 7/1987 |
| JP | 2001-519255 | 10/2001 |
| JP | 2005-507011 | 3/2005 |
| JP | 2008-530309 | 8/2008 |
| JP | 2018-515625 | 6/2018 |
| WO | WO 2006/086758 | 8/2006 |
| WO | WO 2011-050121 | 4/2011 |
| WO | WO 2014-051523 | 4/2014 |
| WO | WO 2017-173040 | 10/2017 |
| WO | WO 2017-173195 | 10/2017 |

OTHER PUBLICATIONS

Derradji, "Effect of silane surface modified titania nanoparticles on the thermal, mechanical, and corrosion protective properties of a bisphenol-A based phthalonitrile resin," Progress in Organic Coatings, 2016, vol. 90, pp. 34-43.
Derradji, "High performance ceramic-based phthalonitrile micro and nanocomposites," Materials Letters, 2016, vol. 182, pp. 380-385.
Derradji, "New oligomeric containing aliphatic moiety phthalonitrile resins: their mechanical and thermal properties in presence of silane surface-modified zirconia nanoparticles," Iranian Polymer Journal, 2016, vol. 25, No. 6, pp. 503-514.
Derradji, "Thermal and Mechanical Properties Enhancements Obtained by Reinforcing a Bisphenol-A Based Phthalonitrile Resin With Silane Surface-Modified Alumina Nanoparticles," Polymer Composites, 2017, pp. 1549-1558.
Dominguez, "Low-melting Phthalonitrile Oligomers: Preparation, Polymerization and Polymer Properties," High Performance Polymers, 2006, vol. 18, No. 3, pp. 283-304.
Dominguez, "Properties of phthalonitrile monomer blends and thermosetting phthalonitrile copolymers," Polymer, 2007, vol. 48, No. 1, pp. 91-97.
Hamciuc, "Poly(1,3,4-oxadiazole-ether-imide)s and their polydimethylsiloxane-containing copolymers," European Polymer Journal, 2007, vol. 43, No. 11, pp. 4739-4749, XP022318829.
Hamciuc, "Poly(ether-imide) and poly (ether-imide)-polydimethylsiloxane containing isopropylidene groups," Polymer Bulletin, 2008, vol. 59, pp. 825-832. XP019561586.
Hsiao, "Synthesis and Characterization of Polyimides Based on Isopropylidene-containing Bis(ether anhydride)s," Journal of Polymer Research, 1997, vol. 4, No. 3, pp. 183-190, XP019221958.
Keller, "High temperature resorcinol-based phthalonitrile polymer," Polymer, 2005, vol. 46, pp. 4614-4618.
Laskoski, "Improved Synthesis of Oligomeric Phthalonitriles and Studies Designed for Low Temperature Cure," Polymer Chemistry, 2014, vol. 52, pp. 1662-1668. XP055380215.
Laskoski, "Synthesis and Properties of a Bisphenol A Based Phthalonitrile Resin," Journal of Polymer Science, Part A: Polymer Chemistry, 2005, vol. 43, No. 18, pp. 4136-4143.
McKeown, "The Synthesis of Symmetrical Phthalocyanines," The Porphyrin Handbook, Phthalocyanines: Synthesis, 2003, vol. 15, pp. 61-124.
Sharman, "Synthesis of Phthalocyanine Precursors," The Porphyrin Handbook, Phthalocyanines: Synthesis, 2003, vol. 15, p. 1-60.
Takekoshi, "Synthesis of High Performance Aromatic Polymers via Nucleophilic Nitro Displacement Reaction," Polymer Journal, 1987, vol. 19, No. 1, pp. 191-202.
Zhou, "Study on One Phthalonitrile Resin System Suitable for RTM Process," ECCM15—15th European Conference on Composite Materials, Venice, Italy, Jun. 24-28, 2012, pp. 1-8.
International Search report for PCT International application No. PCT/US2017/24947 dated Jun. 21, 2017, 3 Pages.
International Search report for PCT International application No. PCT/US2017/024006 dated Jun. 6, 2017, 5 Pages.
International Search report for PCT International application No. PCT/US2017/025233, dated Jun. 19, 2017, 5 Pages.

* cited by examiner

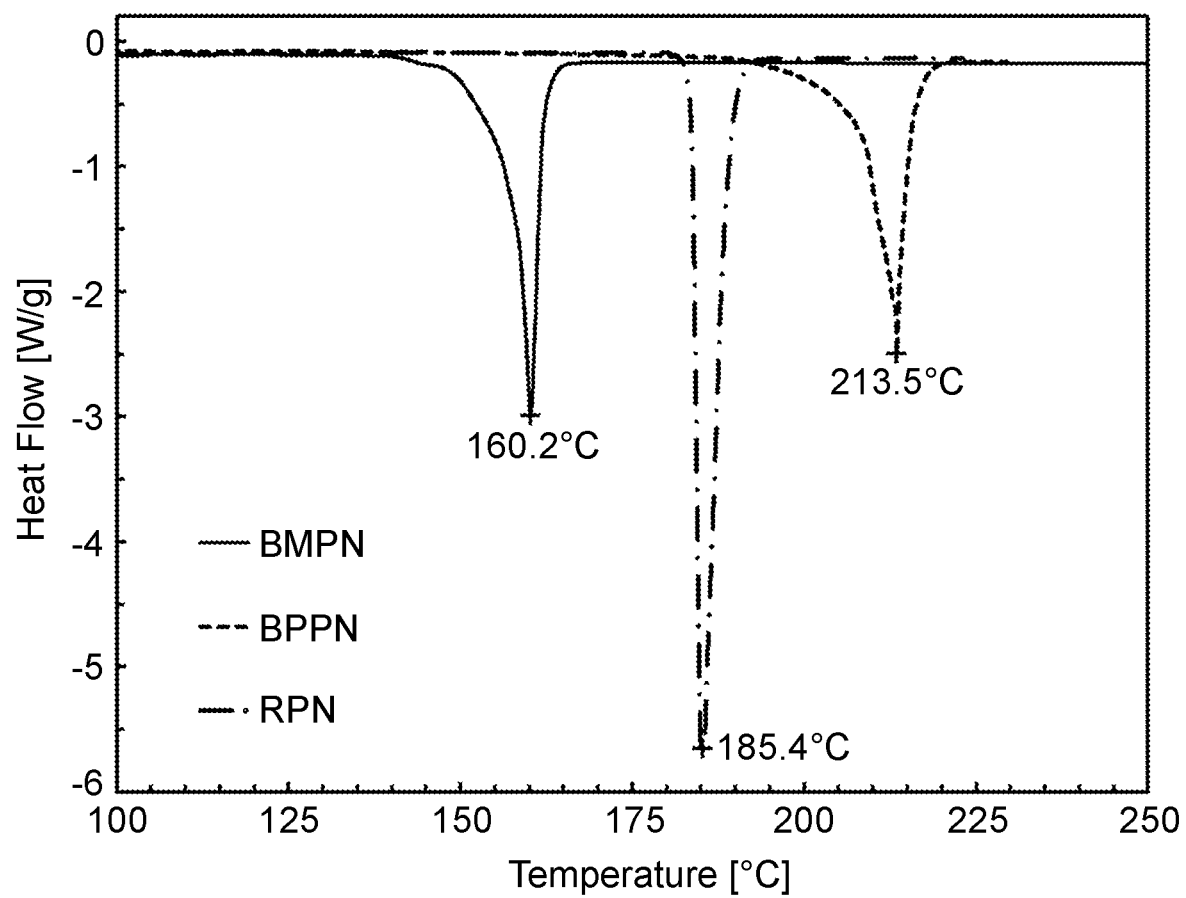

BISPHENOL M DIPHTHALONITRILE ETHER RESIN, BISPHENOL P DIPHTHALONITRILE ETHER RESIN, METHODS OF MAKING SAME, RESIN BLENDS, AND TWO COMPONENT SYSTEMS

CROSS REFERENCE TO RELATED APPLICATIONS

This application is a national stage filing under 35 U.S.C. 371 of PCT/US2017/024006, filed Mar. 24, 2017, which claims the benefit of U.S. Application No. 62/316,248, filed Mar. 31, 2016, U.S. Application No. 62/348,477, filed Jun. 10, 2016, and U.S. Application No. 62/475,396, filed Mar. 23, 2017, the disclosures of which are incorporated by reference in their entirety herein.

FIELD

The present disclosure relates to resins and resin blends, including bisphenol diphthalonitrile ether resins.

BACKGROUND

Temperature resistant polymer networks are critical for an increasing number of industrial market applications. Applications are diverse from building and construction, electronics packaging, energy and power generation, and transportation. As the environmental temperature of an application increases, the number of available materials able to meet requirements shrinks rapidly.

Phthalonitrile (PN) resins are a class of network forming resins that when polymerized supply excellent thermal stability and degradation resistance, yet commercialization of phthalonitrile resin technology and use is hindered by poor processing properties, high cost, and high temperature autoclave cures. Phthalonitrile resins have high melt temperatures due to the rigid structure of many phthalonitrile molecules which incorporate a large percentage of aromatic structures to maintain the thermal performance of the phthalonitrile polymerized network. The phthalonitrile moiety is also rigid and planar and has a tendency to crystallize. These molecular structure attributes contribute to the high melt temperature of multifunctional PN resins. The high cost of the resin is driven by resin synthesis which utilizes higher cost starting materials (similar to anhydride and imide resins) and multistep synthesis routes. A high glass transition temperature of the polymerized resin imparts excellent thermal stability at high service temperatures, but also contributes to the need for high temperature multistep autoclave cures under inert atmosphere to achieve near full conversion.

SUMMARY

Resins and resin blends are described that provide improved processing (i.e., lower melt temperature, wider processing temperature window) and polymer network formation (i.e., lower polymerization temperature, out-of-autoclave polymerization reaction, lower network glass transition temperature) of diphthalonitrile ether resins. In a first aspect, a monomer is provided of Formula I:

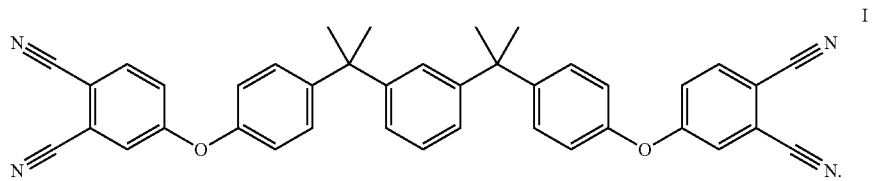 [SMILES: CC(C)(c1ccc(Oc2ccc(C#N)c(C#N)c2)cc1)c1cccc(C(C)(C)c2ccc(Oc3ccc(C#N)c(C#N)c3)cc2)c1]

In a second aspect, a monomer is provided of Formula II:

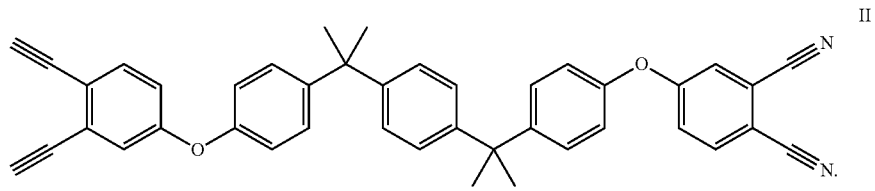 [SMILES: C#Cc1ccc(Oc2ccc(C(C)(C)c3ccc(C(C)(C)c4ccc(Oc5ccc(C#N)c(C#N)c5)cc4)cc3)cc2)cc1C#C]

In a third aspect, a composition is provided including a primary amine curative and a monomer of Formula I.

In a fourth aspect, a polymerized product is provided of the monomer of Formula I.

In a fifth aspect, a composition is provided including a primary amine curative and a monomer of Formula II.

In a sixth aspect, a polymerized product is provided of the monomer of Formula II.

In a seventh aspect, a method of making a polymerized network is provided. The method includes obtaining a monomer of Formula I or Formula II; blending the monomer with a curative, a catalyst, or a combination thereof to form a monomer blend; and subjecting the monomer blend to a temperature of no more than 300 degrees Celsius to form a fully polymerized network. Any optional postcuring of the polymerized network consists of subjecting the polymerized network to a temperature of no more than 300 degrees Celsius.

In an eighth aspect, a two component system is provided. The two component system includes a first component comprising a monomer of Formula I or Formula II; and a second component comprising a curative.

In a ninth aspect, a resin blend is provided. The resin blend includes a blend of at least two monomers selected from the monomers of Formula I, Formula II, and Formula III:

a component of PN resin blends provides for improved processing, polymerization and end use properties of PN cured polymer networks.

BRIEF DESCRIPTION OF THE DRAWINGS

FIG. 1 is a graph of differential scanning calorimetry measurements of PN resins at a thermal ramp rate of 10° C./min: BMPN (solid line), BPPN (dash line), and RPN (dot-dash line).

DETAILED DESCRIPTION

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "a", "an", and "the" are used interchangeably with "at least one" to mean one or more of the elements being described.

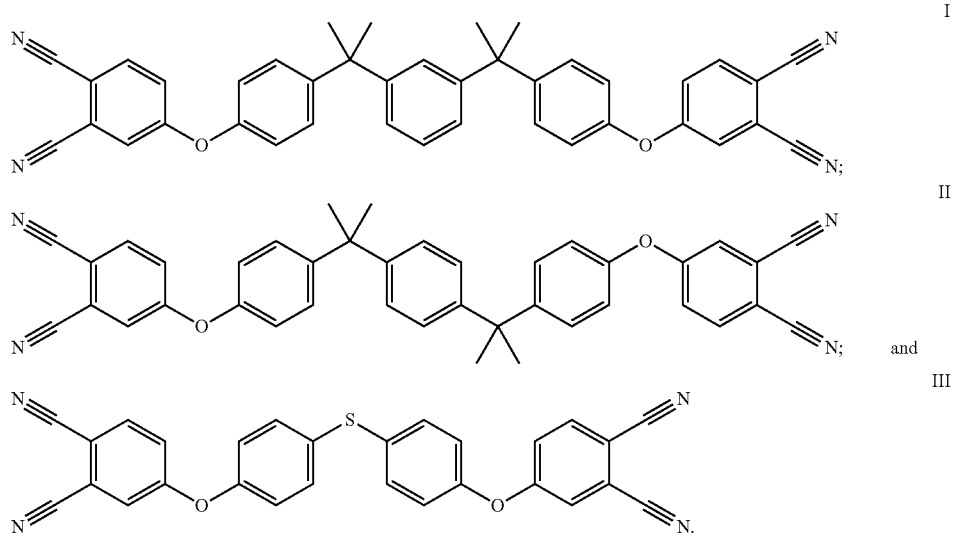

Temperature resistant polymer networks are critical for an increasing number of market applications. As the environmental temperature of an application increases, the number of available materials able to meet requirements shrinks rapidly. The present resins are useful for applications in which a temperature resistant polymer is beneficial.

It was discovered that there remains a need for improving processing and polymerization of phthalonitrile resins. The present disclosure overcomes difficulties noted for processing phthalonitrile resins, such as high melt temperatures, and polymerization of phthalonitrile resins, such as high polymerization temperatures requiring an inert atmosphere autoclave. The use of the monomer resins of Formula I and Formula II as higher molecular weight phthalonitrile (PN) reactive monomer resins as single component resins and as The term "and/or" means either or both. For example "A and/or B" means only A, only B, or both A and B.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in some embodiments," "in certain embodiments," "in one embodiment," "in many embodiments" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

As used herein, the term "phthalonitrile" is inclusive of compounds having the characteristic benzene derivative having two adjacent nitrile groups. In the illustrated phthalonitrile group, R is for instance and without limitation, ether, thioether, aryl, alkyl, halogen, amine, ester, or amide, heteroalkyl, or (hetero)hydrocarbyl.

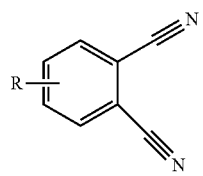

As used herein, "bisphenol M diphthalonitrile ether" refers to bis(3,4-dicyanophenyl) ether of bisphenol M.

As used herein, "bisphenol T diphthalonitrile ether" refers to bis(3,4-dicyanophenyl) ether of bisphenol T.

As used herein, "bisphenol P diphthalonitrile ether" refers to bis(3,4-dicyanophenyl) ether of bisphenol P.

As used herein, "resorcinol diphthalonitrile ether" refers to bis(3,4-dicyanophenyl) ether of resorcinol.

As used herein, "alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

As used herein, the term "heteroalkyl" includes both straight-chained, branched, and cyclic alkyl groups with one or more heteroatoms independently selected from S, O, Si, P, and N, and both unsubstituted and substituted alkyl groups. Unless otherwise indicated, the heteroalkyl groups typically contain from 1 to 20 carbon atoms. "Heteroalkyl" is a subset of "hetero(hetero)hydrocarbyl" described below. Examples of "heteroalkyl" as used herein include, but are not limited to, methoxy, ethoxy, propoxy, 3,6-dioxaheptyl, 3-(trimethylsilyl)-propyl, 4-dimethylaminobutanyl, and the like. Unless otherwise noted, heteroalkyl groups may be mono- or polyvalent.

As used herein, "aryl" is an aromatic group containing 6-18 ring atoms and can contain fused rings, which may be saturated, unsaturated, or aromatic. Examples of an aryl group include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

As used herein, "(hetero)hydrocarbyl" is inclusive of (hetero)hydrocarbyl alkyl and aryl groups, and hetero(hetero)hydrocarbyl heteroalkyl and heteroaryl groups, the later comprising one or more catenary oxygen heteroatoms such as ether or amino groups. Hetero(hetero)hydrocarbyl may optionally contain one or more catenary (in-chain) functional groups including ester, amide, urea, urethane and carbonate functional groups. Unless otherwise indicated, the non-polymeric (hetero)hydrocarbyl groups typically contain from 1 to 60 carbon atoms. Some examples of such (hetero)hydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl" and "heteroaryl" supra.

As used herein, the term "polymerized product" refers to the result of a polymerization reaction of a polymerizable composition.

As used herein, the term "residue" is used to define the (hetero)hydrocarbyl portion of a group remaining after removal (or reaction) of the attached functional groups, or the attached groups in a depicted formula. For example, the "residue" of butyraldehyde, $C_4H_9$—CHO is the monovalent alkyl $C_4H_9$—. The residue of phenylene diamine $H_2N$—$C_6H_4$—$NH_2$, is the divalent aryl —$C_6H_4$—.

Various exemplary embodiments of the disclosure will now be described. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

The present disclosure is generally directed to diphthalonitrile ether resins (e.g., monomers), resin blends, two component systems, and methods of making the same.

Phthalonitriles are an ideal precursor resin for bulk polymerization reactions due to the addition nature of the phthalonitrile polymerization, advantageous for avoiding unbound reaction byproducts that can weaken the network, leach out of the network, and volatilize at high temperatures. Phthalonitriles undergo an addition cure reaction when promoted by a catalyst or curative. Known catalyst systems for phthalonitrile polymerization promote the tetracyclization of four phthalonitrile moieties into a phthalocyanine ring (McKeown, N. B., *The Synthesis of Symmetrical Phthalocyanines*, in *The Porphyrin Handbook*, K. M. Kadish, K. M. Smith, and R. Guilard, Editors. 2003, Academic Press: Amsterdam. p. 61-124). The phthalocyanines can exist in one of two forms: the metal free (PcH2) or the metal containing (PcM) phthalocyanine. PcH2 may be formed from the addition of base, an alcohol, and heat, or the addition of a suitable reducing agent and heat. These conditions may be satisfied through the addition of an amine base with a primary alcohol (e.g. C1-C5 alcohols). The base catalyzes the formation of a PcH2 and the oxidation of an alcohol to an aldehyde. A suitable reducing agent (e.g., hydroquinone or 1,2,3,6-tetrahydropyridine) able to supply the two electrons and two protons formally needed for PcH2 formation will also lead to cyclotetramerization. PcM may be formed by the addition of metal, organometals or metal salts and heat. The metals coordinate with the central four nitrogens of the phthalocyanine ring. Depending on the coordination state, a metal may interact with more than one phthalocyanine ring giving rise to stacked phthalocyanine structures. Many metals have been shown to result in cyclotetramerization (ibid.). The downside of these catalyst systems for bulk polymerization reactions is often the evolution of volatiles.

In the absence of a primary alcohol able to undergo oxidation to an aldehyde, primary amines act as phthalonitrile curatives and give rise to an N-substituted-poly(3-iminoisoindolenine) linked polymer network when a multifunctional phthalonitrile resin is employed (U.S. Pat. No. 4,408,035 (Keller) and U.S. Pat. No. 4,223,123 (Keller et al.)). The lack of an alcohol is believed to hinder the formation of PcH2 phthalocyanine ring. Primary amines that have shown good reactivity with phthalonitriles are based on aniline. Higher molecular weight and lower volatility aniline functional curatives are typically desired to avoid loss of the curative during polymerization. Dianiline based curatives can be of value due to a higher aniline functionality per weight of the curative. Example dianiline based curatives that will promote phthalonitrile polymerization include for instance and without limitation, 4,4'-(1,3-phenylenedioxy)dianiline, 4,4'-(1,4-phenylenedioxy)dianiline, bis[4-(4-aminophenoxy)phenyl]sulfone, 4,4'-(4,4'-isopropylidenediphenyl-1,1'-diyldioxy)dianiline, 4,4'-(1,3-phenylenediisopropylidene)dianiline, 4,4'-(1,4-phenylenediisopropylidene)dianiline, 4,4'-(1,1'-biphenyl-4,4'-diyldioxy)dianiline, 4,4'-methylenedianiline, 4,4'-sulphonyldianiline, 4,4'-methylene-bis(2-methylaniline), 3,3'-methylenedianiline, 3,4'-methylenedianiline, 4,4'-oxydianiline, 4,4'-(isopropylidene)dianiline, 4,4'-(hexafluoroisopropylidene)dianiline, 4,4'-(hexafluoroisopropylidene)bis(p-phenyleneoxy)dianiline, and 4,4'-diaminobenzophenone. The primary amine promoted phthalonitrile cure reaction proceeds at an appreciable rate between temperatures of 200° C. to 250° C. Amine cured phthalonitrile polymerized networks have demonstrated excellent thermal stability imparted by a high glass transition temperature, good thermal and thermoxidative degradation resistance, plus are inherently non-flammable, and have low moisture uptake. However, current resin technology is limited by long high temperature multistep autoclave cure schedules due to a high glass transition temperature of over 400° C. (U.S. Pat. No. 4,223,123 (Keller et al.)).

Resorcinol diphthalonitrile ether (RPN) has achieved commercial significance and offers a melt temperature of 185° C. and a low melt viscosity, compared to other higher molecular weight phthalonitrile resins. An RPN cured network exhibits a high glass transition temperature of over 450° C. (U.S. Pat. No. 4,587,325 (Keller); and Keller, T. M. and D. D. Dominguez, High temperature resorcinol-based phthalonitrile polymer. Polymer, 2005. 46(13): p. 4614-4618). Bisphenol A diphthalonitrile ether (BAPN) is another well-known resin with a melt temperature of 198° C. (U.S. Pat. No. 4,223,123 (Keller et al.)). A BAPN cured network also exhibits a high glass transition temperature of over 450° C. (Laskoski, M., D. D. Dominguez, and T. M. Keller, *Synthesis and properties of a bisphenol A based phthalonitrile resin*. Journal of Polymer Science Part A: Polymer Chemistry, 2005. 43(18): p. 4136-4143). Biphenol diphthalonitrile (BPN) has a melt temperature of 233° C., and the cured BPN network exhibits a glass transition temperature over 450° C. (Dominguez, D. D. and T. M. Keller, *Properties of phthalonitrile monomer blends and thermosetting phthalonitrile copolymers*. Polymer, 2007. 48(1): p. 91-97; and U.S. Pat. No. 4,587,325 (Keller)). The high glass transition temperature ($T_g$) of each of the RPN, BAPN, and BPN cured networks necessitates a multistep cure procedure up to 425° C. under inert autoclave conditions to overcome vitrification hindering polymer network formation and to minimize network degradation at cure temperatures above 300° C. Phthalonitrile resin technology is needed that results in liquid PN resins at temperatures below 200° C. that form polymer networks with lower glass transition temperatures that avoid vitrification and enable out-of-autoclave cure at lower temperatures without the need of an inert atmosphere.

The present disclosure describes bisphenol M diphthalonitrile (BMPN) resin as a low melt temperature, low viscosity phthalonitrile resin displaying supercooled liquid properties. BMPN is demonstrated to be capable of out of autoclave (OOA) cure to yield a network polymer with a surprisingly low glass transition temperature, as compared to previously known PN network polymers that are slower reacting and require cure at higher temperatures under an inert atmosphere in an autoclave. The present disclosure also describes bisphenol P diphthalonitrile (BPPN) resin as a higher melting phthalonitrile resin. BPPN lacks the favorable processing properties (e.g., low melt temperature and supercool liquid) of BMPN, but BPPN does enable an OOA cure procedure and a low glass transition temperature polymer network, as compared to previous PN resin technology.

The synthesis of multifunctional phthalonitrile monomer resins from the nucleophilic substitution of 4-nitrophthalonitrile with a multifunctional phenolic monomer resin is a known method for the production of phthalonitrile resins (U.S. Pat. No. 4,304,896 (Keller et al.)). The substitution reaction is promoted by the addition of a base in an aprotic polar solvent. Sodium carbonate, potassium carbonate, cesium carbonate are preferred bases; metal hydroxide bases will also promote the substitution reaction. Polar solvents such as dimethylforamide, acetamide, dimethylsulfoxide, N-methylpyrrolidone are generally preferred solvents; other solvents include acetone, acetonitrile, methylethylketone, methylisobutylketone. The nucleophilic substitution reaction of the nitro substituent by a phenoxy anion will proceed at ambient temperature and can be modestly accelerated by higher temperatures. Synthesis of either BMPN or BPPN has not been reported, however.

In a first aspect, a monomer is provided of Formula I:

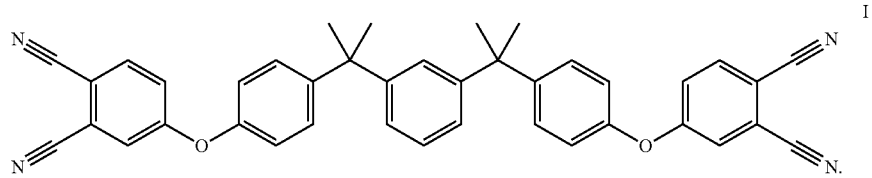 [SMILES: CC(C)(c1ccc(Oc2ccc(C#N)c(C#N)c2)cc1)c1cccc(C(C)(C)c2ccc(Oc3ccc(C#N)c(C#N)c3)cc2)c1]

I

The monomer of Formula I may also be referred to as the bis(3,4-dicyanophenyl) ether of bisphenol M. In a second aspect, a composition is provided including a primary amine curative and a monomer of Formula I. In a third aspect, a polymerized product is provided of the monomer of Formula I. In certain embodiments, the polymerized product exhibits a glass transition temperature between 200 to 250 degrees Celsius.

In a fourth aspect, a monomer is provided of Formula II:

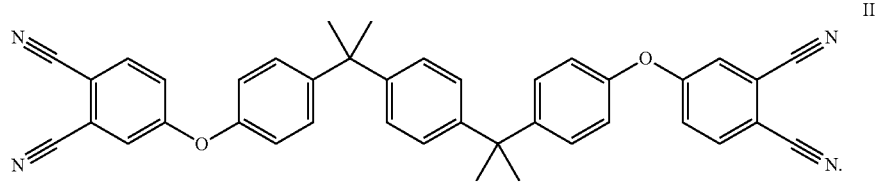

II

The monomer of Formula II may also be referred to as the bis(3,4-dicyanophenyl) ether of bisphenol P. In a fifth aspect, a composition is provided including a primary amine curative and a monomer of Formula II. In a sixth aspect, a polymerized product is provided of the monomer of Formula II. In certain embodiments, the polymerized product exhibits a glass transition temperature of 250 to 300 degrees Celsius.

More particularly, the synthesis of BMPN and BPPN is demonstrated in the present disclosure by the nucleophilic substitution of the nitro group of 4-nitrophthalonitrile by phenolic residues of the bisphenols catalyzed by potassium carbonate in DMSO. The reaction was conducted at ambient temperature under a nitrogen atmosphere. Each resin was precipitated by the addition of the reaction solution to a low molecular weight alcohol (e.g. methanol, ethanol, propanol, of which methanol may be preferred) leaving undissolved salts behind in the reaction vessel. The precipitated product was collected by vacuum filtration and washed with water to remove residual reaction salts and methanol to dry the product. The product was dried under reduced pressure and elevated temperature. All residual solvent was removed by a vacuum bake of the resin at an upper temperature of 200° C.; higher temperatures were used for higher melt temperature resins.

The structure of the BMPN appeared to greatly suppress the melt temperature of the phthalonitrile when compared to BPPN and other phthalonitrile resins. The reduction in melt temperature is dramatic when comparing BMPN to BPPN. The BMPN and BPPN resins are isomers and differ in structure by the connectivity at the central phenyl ring, BMPN having meta connectivity on the central phenyl ring (see Formula I above) and BPPN having para connectivity on the central phenyl ring (see Formula II above). Unexpectedly, the difference in connectivity translates into a melt temperature of 160° C. for BMPN compared to 213° C. for BPPN, as shown in FIG. 1. The melt temperature of BMPN is lower than other reported bisphenol phthalonitriles (Takekoshi, T., Synthesis of High Performance Aromatic Polymers via Nucleophilic Nitro Displacement Reaction. Polym J, 1987. 19(1): p. 191-202).

Interestingly, BMPN displays the ability to exist as a supercooled liquid at temperatures below its melt temperature, a property that has not been displayed by other bisphenol based phthalonitrile resins. This attribute adds a processing advantage to BMPN by enabling liquid resin processing at temperatures below the melt temperature, providing a larger delta T between the cure exotherm of the resin and the resin melt temperature. A larger delta T provides a greater processing window and longer gel times for a BMPN resin system (e.g., BMPN with a curative or catalyst added) compared to other phthalonitrile resin systems. This supercooled liquid property has been exemplified, as detailed below in Example 1, through monitoring the resin viscosity at a temperature, 135° C., below the resin melt temperature. The measurements demonstrated the slow crystallization time of the BMPN resin under different flow sampling conditions and the use of short duration low shear flow as a means of maintaining the supercooled liquid state. When applying these measurements to RPN and BPPN, these resins crystallized as the environmental temperature was reduced below the resin melt temperature, showing that these resins do not exhibit supercooled liquid properties. The polymerization of each of BMPN, BPPN and RPN was initiated by the addition of 4 parts per hundred (pph) by weight of 4,4'-(1,3-phenylenedioxy)dianiline. The lower melt temperature and supercooled liquid properties of the BMPN resin enabled the addition of the curative at a resin temperature of 135° C. The higher melt temperature of BPPN required the curative to be added at a resin temperature of 225° C. The curative was added to RPN at a temperature of 200° C. The cure conditions of the resins are detailed in the Examples below.

The BMPN and BPPN cured networks surprisingly display significantly lower glass transition temperatures as compared to previous PN cured resins. The BMPN cured network displays a glass transition temperature of 209° C. as indicated by E' onset and 229° C. as indicated by tan δ peak temperature. The BPPN cured network displays a glass transition temperature of 264° C. as indicated by E' onset and 287° C. as indicated by tan δ peak temperature. Direct comparison of the BMPN and BPPN cured networks shows the impact of the meta verses para connectivity between the resin isomers, since the crosslink density between the two networks was similar due to the molecular weight of the resins being the same.

The low $T_g$ of each of the BMPN and BPPN cured networks enabled cure of the two resins to be completed at temperatures below 300° C. without the use of an autoclave. Post cures at higher temperatures did not produce an increase in the glass transition temperature of the networks. Comparatively, RPN requires post cure temperatures over 300° C. under an inert atmosphere. The RPN network was post cured to a final cure of temperature of 450° C. in an inert atmosphere tube furnace. A glass transition temperature by E' onset was measured to be 412° C. A peak in the mechanical tan δ was not observed and may exist at higher temperature. The lower $T_g$ of the BMPN and BPPN cured networks avoided vitrification (a loss of translational segment mobility) when cured at temperatures below 300° C. Vitrification is a common problem among PN resins, and limits complete cure of a resin as the glass transition temperature of the incomplete cured resin network exceeds the external cure temperature. Complete cure of the BMPN and BPPN resins was accomplished at an upper cure temperature of 250° C. and 300° C., respectively, under OOA conditions.

Accordingly, in a seventh aspect, a method of making a polymerized network is provided. The method includes obtaining a monomer of Formula I or Formula II; blending the monomer with a curative, a catalyst (e.g., a base such as 1,5-diazabicyclo(4.3.0)non-5-ene or 1,8-diazabicyclo[5.4.0] undec-7-ene; reducing agents such as hydroquinone and 1,2,3,6-tetrahydropyridine; metal, organometals or metal salts such as copper, iron, copper acetylacetonate, zinc naphthenate, dibutyltin dilaurate, stannous chloride, stannic chloride, copper chloride, iron chloride, and/or calcium carbonate), or a combination thereof to form a monomer blend (or resin blend); and subjecting the monomer blend to a temperature of no more than 300 degrees Celsius to form a fully polymerized network. Generally, the composition is heated to a temperature between about 50° C. and 300° C., such as between about 130-300° C., for a time of about 1-480 minutes. Suitable sources of heat include induction heating coils, ovens, hot plates, heat guns, infrared sources including lasers, microwave sources.

Solvents can be used as a processing aid. Useful solvents are ketones such as acetone, methyl ethyl ketone, methyl isobutyl ketone, cyclopentanone and cyclohexanone; amides such as acetamide, formamide, N,N-dimethylforamide, N-methylpyrrolidinone; sulfones such as tetramethylene sulfone, 3-methylsulfolane, 2,4-dimethylsulfolane, butadiene sulfone, methyl sulfone, ethyl sulfone, propyl sulfone, butyl sulfone, methyl vinyl sulfone, 2-(methylsulfonyl)ethanol, 2,2'-sulfonyldiethanol; sulfoxides such as dimethyl sulfoxide; cyclic carbonates such as propylene carbonate, ethylene carbonate and vinylene carbonate; carboxylic acid esters such as ethyl acetate, methyl cellosolve acetate, methyl formate; and other solvents such as tetrahydrofuran, methylene chloride, dichloromethane, chloroform, acetonitrile, nitromethane, glycol sulfite and 1,2-dimethoxyethane (glyme).

An advantage to at least certain embodiments of the method is that any optional postcuring of the polymerized network is free of subjecting the polymerized network to a temperature greater than 300 degrees Celsius. Stated another way, in some embodiments of the method all optional postcuring of the polymerized network includes subjecting the polymerized network to temperatures of no more than 300 degrees Celsius. In some embodiments of the method the monomer is of Formula I and the monomer blend is subjected to a temperature of no more than 250 degrees Celsius. Moreover, another advantage to at least certain embodiments of the method is that the curing, postcuring, or both are conducted in air (e.g., in out of autoclave conditions and need not be conducted in an inert atmosphere). In some embodiments of the method the monomer blend is subjected to a temperature of no more than 300 degrees Celsius in air. Optionally, the monomer blend is subjected to a temperature of no more than 300 degrees Celsius at ambient pressure.

The cured BMPN and BPPN networks were discovered to possess the high temperature thermal and thermo-oxidation degradation resistance characteristic of phthalonitrile cured networks. Thermal degradation was characterized by thermal gravimetric analysis under thermal ramp heating conditions at a temperature ramp rate of 10° C./min. The degradative weight loss of BMPN and BPPN cured networks under air and inert nitrogen are detailed in the Examples below. The degradative weight loss of a RPN cured network is also shown for comparison. All resins were cured with 4 pph of 4,4'-(1,3-phenylenedioxy)dianiline. Under a non-oxidative environment (e.g., nitrogen), the BMPN and BPPN networks experienced a weight loss of five percent at 478° C. and 477° C., respectively. The RPN network was slightly higher at 497° C. Under an oxidative environment (e.g., air), the temperature for five percent weight loss was 489° C. for both the BMPN and BPPN network. The temperature for five percent weight loss was 507° C. for RPN under air. The temperatures under air were higher than under nitrogen due to the effect of oxygen adding to the resin, leading to a higher temperature for a similar weight loss in a thermo-oxidative environment compared to a thermal environment.

Compositions according to at least certain embodiments of the disclosure include one or more curatives. Such curatives often include an amine compound, such as a primary amine, for instance including an aniline functional residue. Combinations of various curatives can be used if desired. The curative is typically present in an amount of at least 1 percent by weight of the resin blend, at least 2 percent, at least 5 percent, at least 10 percent, at least 15 percent or even at least 20 percent by weight of the resin blend; and up to 40 percent by weight of the resin blend, up to 35 percent, up to 30 percent, or even up to 25 percent by weight of the resin blend; such as between 0 and 40 percent by weight of the resin blend. Example dianiline based curatives that will promote phthalonitrile polymerization include for instance and without limitation, 4,4'-(1,3-phenylenedioxy)dianiline, 4,4'-(1,4-phenylenedioxy)dianiline, bis[4-(4-aminophenoxy)phenyl]sulfone, 4,4'-(4,4'-isopropylidenediphenyl-1,1'-diyldioxy)dianiline, 4,4'-(1,3-phenylenediisopropylidene)dianiline, 4,4'-(1,4-phenylenediisopropylidene)dianiline, 4,4'-(1,1'-biphenyl-4,4'-diyldioxy) dianiline, 4,4'-methylenedianiline, 4,4'-sulphonyldianiline, 4,4'-methylene-bis(2-methylaniline), 3,3'-methylenedianiline, 3,4'-methylenedianiline, 4,4'-oxydianiline, 4,4'-(isopropylidene)dianiline, 4,4'-(hexafluoroisopropylidene)dianiline, 4,4'-(hexafluoroisopropylidene)bis(p-phenyleneoxy)dianiline, 4,4'-diaminobenzophenone.

In an eighth aspect, a two component system is provided. A two component system allows for the monomer and the curative to be included in separate components, thus the two component system comprises a first component comprising a monomer of Formula I or Formula II; and a second component comprising a curative. Prior to use, the two components are typically blended together. Other materials are optionally included in the two component system. In certain embodiments, the first component, the second component, or both, further comprises at least one additive. The one or more additives can be independently selected from a toughener, a filler, or a combination thereof. Suitable additives are described further below.

In a ninth aspect, a resin blend is provided. The resin blend includes a blend of at least two monomers selected from the monomers of Formula I, Formula II, and Formula III:

of bisphenol A, bis(3,4-dicyanophenyl) ether of bisphenol AP, bis(3,4-dicyanophenyl) ether of bisphenol AF, bis(3,4-dicyanophenyl) ether of bisphenol B, bis(3,4-dicyanophenyl) ether of bisphenol BP, bis(3,4-dicyanophenyl) ether of bisphenol C, bis(3,4-dicyanophenyl) ether of bisphenol C2, bis(3,4-dicyanophenyl) ether of bisphenol E, bis(3,4-dicyanophenyl) ether of bisphenol F, bis(3,4-dicyanophenyl) ether of 3,3',5,5'-tetramethylbisphenol F, bis(3,4-dicyanophenyl) ether of bisphenol FL, bis(3,4-dicyanophenyl) ether of bisphenol G, bis(3,4-dicyanophenyl) ether of bisphenol S, bis(3,4-dicyanophenyl) ether of bisphenol P, bis(3,4-dicyanophenyl) ether of bisphenol PH, bis(3,4-dicyanophenyl) ether of bisphenol TMC, bis(3,4-dicyanophenyl) ether of bisphenol Z, bis(3,4-dicyanophenyl) ether of 4,4'-dihydroxybiphenyl, bis(3,4-dicyanophenyl) ether of 4,4'-dihydroxydiphenyl ether, bis(3,4-dicyanophenyl) ether of catechol, bis(3,4-dicyanophenyl) ether of 4,4'-dihydroxybenzophenone, 3,4-dicyanophenyl ether of phenol, 2,3-dicyanophenyl ether of phenol, 4-tert-butylphthalonitrile, 4-butoxyphthalonitrile, 3,4-dicyanophe-

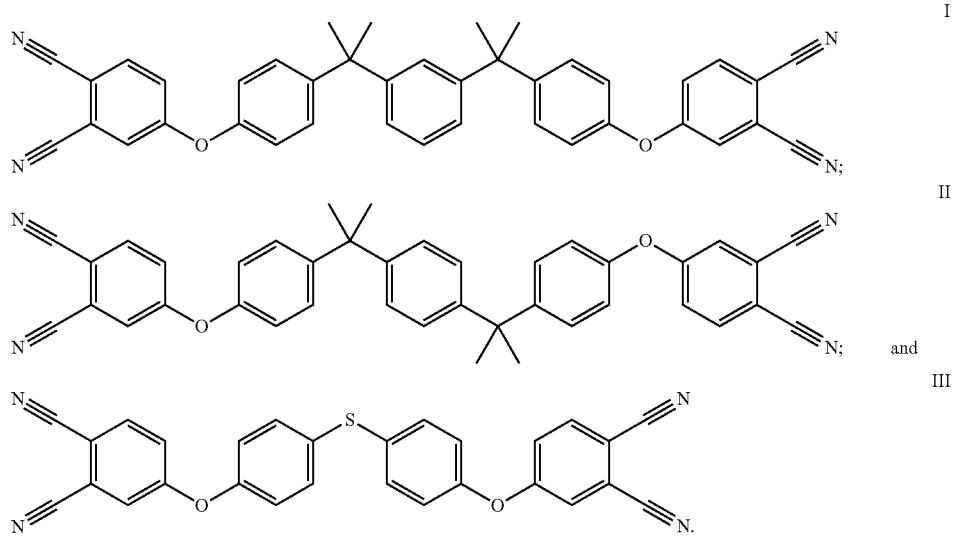

I

II and

III

The monomer of Formula III may also be referred to as the bis(3,4-dicyanophenyl) ether of bisphenol T. In certain embodiments, the resin blend comprises a blend of the monomer of Formula I and the monomer of Formula II. In certain embodiments, the resin blend comprises a blend of the monomer of Formula I and the monomer of Formula III. Similarly, in certain embodiments, the resin blend comprises a blend of the monomer of Formula II and the monomer of Formula III. The weight ratio of two monomers in the resin blend is not particularly limited. For instance, the weight ratio of the monomer of Formula I to the monomer of Formula II, or of the monomer of Formula I to the monomer of Formula III, or of the monomer of Formula II to the monomer of Formula III, typically ranges from 10:90 to 90:10, inclusive. In select embodiments, the resin blend comprises a blend of each of the monomers of Formula I, Formula II, and Formula III.

In certain embodiments, resin blends according to the present disclosure further comprises at least one additional phthalonitrile resin. Example additional phthalonitrile resins include for instance and without limitation bis(3,4-dicyanophenyl) ether of bisphenol A, bis(2,3-dicyanophenyl) ether nyl ether of 4-cumylphenol, 3,4-dicyanophenyl ether of 2-allylphenol, 3,4-dicyanophenyl ether of eugenol. Typically the resin blend (of two or more resins) is a solid at 25° C.

Certain other optional additives may also be included in compositions, two component systems, and/or resin blends according to the present disclosure, including, for example, tougheners, fillers, and combinations thereof. Such additives provide various functions. For instance, a toughening agent such as organic particles, may add strength to the composition after curing without interfering with curing. It will be understood by one of skill in the art that one compound may form two or more different functions. For example, a compound may function as both a toughening agent and a filler. In some embodiments, such additives will not react with the resins of the resin blend. In some embodiments, such additives may include reactive functional groups, particularly as end groups. Examples of such reactive functional groups include, but are not limited to, amines, thiols, alcohols, epoxides, vinyls, and combinations thereof.

Useful toughening agents are polymeric compounds having both a rubbery phase and a thermoplastic phase such as:

graft polymers having a polymerized, diene, rubbery core and a polyacrylate, polymethacrylate shell; graft polymers having a rubbery, polyacrylate core with a polyacrylate or polymethacrylate shell; and elastomeric particles polymerized in situ in the epoxide from free radical polymerizable monomers and a copolymerizable polymeric stabilizer.

Examples of useful toughening agents of the first type include graft copolymers having a polymerized, diene, rubbery backbone or core to which is grafted a shell of an acrylic acid ester or methacrylic acid ester, monovinyl aromatic hydrocarbon, or a mixture thereof, such as disclosed in U.S. Pat. No. 3,496,250 (Czerwinski). Exemplary rubbery backbones include polymerized butadiene or a polymerized mixture of butadiene and styrene. Exemplary shells including polymerized methacrylic acid esters are lower alkyl (C1-C4) substituted methacrylates. Exemplary monovinyl aromatic hydrocarbons are styrene, alpha-methylstyrene, vinyltoluene, vinylxylene, ethylvinylbenzene, isopropylstyrene, chlorostyrene, dichlorostyrene, and ethylchlorostyrene. It is important that the graft copolymer contain no functional groups that would interfere with the polymerization of the resin.

Examples of useful toughening agents of the second type are acrylate core-shell graft copolymers wherein the core or backbone is a polyacrylate polymer having a glass transition temperature below 0° C., such as polybutyl acrylate or polyisooctyl acrylate to which is grafted a polymethacrylate polymer (shell) having a glass transition above 25° C., such as polymethylmethacrylate.

The third class of useful toughening agents includes elastomeric particles that have a glass transition temperature ($T_g$) below 25° C. before mixing with the other components of the composition. These elastomeric particles are polymerized from free radical polymerizable monomers and a copolymerizable polymeric stabilizer. The free radical polymerizable monomers are ethylenically unsaturated monomers or diisocyanates combined with co-reactive difunctional hydrogen compounds such as diols, diamines, and alkanolamines.

Useful toughening agents include core/shell polymers, such as methacrylate-butadiene-styrene (MBS) copolymer wherein the core is crosslinked styrene/butadiene rubber and the shell is polymethylacrylate (for example, those available under the trade names ACRYLOID KM653 and KM680, from Rohm and Haas, Philadelphia, Pa.), those having a core including polybutadiene and a shell including poly(methyl methacrylate) (for example, those available under the trade names KANE ACE M511, M521, B11A, B22, B31, and M901 from Kaneka Corporation, Houston, Tex. and CLEARSTRENGTH C223 from ATOFINA, Philadelphia, Pa.), those having a polysiloxane core and a polyacrylate shell (for example, those available under the trade names CLEARSTRENGTH S-2001 from ATOFINA and GENIOPERL P22 from Wacker-Chemie GmbH, Wacker Silicones, Munich, Germany), those having a polyacrylate core and a poly(methyl methacrylate) shell (for example, those available under the trade names PARALOID EXL2330 from Rohm and Haas and STAPHYLOID AC3355 and AC3395 from Takeda Chemical Company, Osaka, Japan), those having an MBS core and a poly(methyl methacrylate) shell (for example, those available under the trade names PARALOID EXL2691A, EXL2691, and EXL2655 from Rohm and Haas); and the like; and mixtures thereof.

As used above, for acrylic core/shell materials "core" will be understood to be an acrylic polymer having a $T_g$ of less than 0° C. and "shell" will be understood to be an acrylic polymer having a $T_g$ of greater than 25° C.

Other useful toughening agents include: carboxylated and amine terminated acrylonitrile/butadiene vulcanizable elastomer precursors, such as those available under the trade names HYCAR CTBN 1300X8, ATBN 1300X16, and HYCAR 1072 from B. F. Goodrich Chemical Co.; butadiene polymers, such as those available under the trade name HYCAR CTB; amine functional polyethers such as HCl 101 (i.e., polytetramethylene oxide diamine) a 10,000 MW, primary amine-terminated, compound from 3M Co., St. Paul, Minn., and those available under the trade name JEFFAMINE from Huntsman Chemical Co., Houston, Tex. Useful liquid poly-butadiene hydroxyl terminated resins include those available under the trade names LIQUIFLEX H by Petroflex of Wilmington, Del., and HT 45 by Sartomer of Exton, PN.

Tougheners may include epoxy-terminated compounds, which can be incorporated into the polymer backbone. A typical, preferred, list of tougheners includes: acrylic core/shell polymers; styrene-butadiene/methacrylate core/shell polymers; polyether polymers; carboxylated acrylonitrile/butadienes; and carboxylated butadienes. Advantages can be obtained from the provision of the chain extension agent in a composition with an epoxy resin even in the absence of a toughening agent as described above. However, particular advantage is achieved from the presence of the toughening agent or combinations of different agents, as previously suggested.

Various combinations of toughening agents can be used if desired. If used, a toughening agent is present in the resin blend in an amount of at least 3 percent by weight, or at least 5 percent by weight. If used, a toughening agent is present in a resin blend in an amount of no greater than 35 percent by weight, or no greater than 25 weight percent.

Other optional additives, or adjuvants, may be added to the compositions as desired. Examples of such other optional additives include as colorants, anti-oxidant stabilizers, thermal degradation stabilizers, light stabilizers, flow agents, bodying agents, flatting agents, inert fillers, binders, blowing agents, fungicides, bactericides, surfactants, plasticizers, rubber tougheners, and other additives known to those skilled in the art. Such additives are typically substantially unreactive. These adjuvants, if present, or other optional additives, are added in an amount effective for their intended purpose.

Examples of suitable filler materials include reinforcement-grade carbon black, fluoroplastics, clays, and any combination of any of these in any proportions.

The phrase "reinforcement-grade carbon black" as used herein, includes any carbon black with an average particle size smaller than about 10 microns. Some particularly suitable average particle sizes for reinforcement-grade carbon black range from about 9 nm to about 40 nm. Carbon black that is not reinforcement grade include carbon black with an average particle size larger than about 40 nm. Carbon nanotubes are also useful fillers. Carbon black fillers are typically employed as a means to balance, elongation, hardness, abrasion resistance, conductivity, and processibility of compositions. Suitable examples include MT blacks (medium thermal black) designated N-991, N-990, N-908, and N-907; FEF N-550; and large particle size furnace blacks.

Other useful fillers include diatomaceous earth, barium sulfate, talc, silica, calcium carbonate, and calcium fluoride. The choice and amounts of optional components depend on the needs of the specific application.

Various embodiments are provided that include monomers, compositions, polymerization products, methods, two component systems, and resin blends.

Embodiment 1 is a monomer of Formula I:

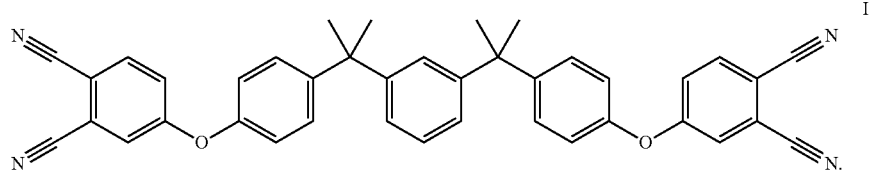 [SMILES: CC(C)(c1ccc(Oc2ccc(C#N)c(C#N)c2)cc1)c1cccc(C(C)(C)c2ccc(Oc3ccc(C#N)c(C#N)c3)cc2)c1]

Embodiment 2 is a composition including a primary amine curative and a monomer of Formula I.

Embodiment 3 is the composition of embodiment 2, further including at least one filler.

Embodiment 4 is the composition of embodiment 2 or embodiment 3, wherein the primary amine curative comprises an aniline functional residue.

Embodiment 5 is the composition of any of embodiments 2 to 4, wherein the primary amine curative is selected from 4,4'-(1,3-phenylenedioxy)dianiline, 4,4'-(1,4-phenylenedioxy)dianiline, bis[4-(4-aminophenoxy)phenyl]sulfone, 4,4'-(4,4'-isopropylidenediphenyl-1,1'-diyldioxy)dianiline, 4,4'-(1,3-phenylenediisopropylidene)dianiline, 4,4'-(1,4-phenylenediisopropylidene)dianiline, 4,4'-(1,1'-biphenyl-4,4'-diyldioxy)dianiline, 4,4'-methylenedianiline, 4,4'-sulphonyldianiline, 4,4'-methylene-bis(2-methylaniline), 3,3'-methylenedianiline, 3,4'-methylenedianiline, 4,4'-oxydianiline, 4,4'-(isopropylidene)dianiline, 4,4'-(hexafluoroisopropylidene)dianiline, 4,4'-(hexafluoroisopropylidene)bis(p-phenyleneoxy)dianiline, 4,4'-diaminobenzophenone, and combinations thereof.

Embodiment 6 is the composition of any of embodiments 2 to 5, wherein the primary amine curative is present in an amount of between 0 and 40 percent by weight of the polymerized product.

Embodiment 7 is the polymerized product of the monomer of Formula I.

Embodiment 8 is the polymerized product of the composition of any of embodiments 2 to 6.

Embodiment 9 is the polymerized product of embodiment 8, wherein the product exhibits a glass transition temperature between 200 to 250 degrees Celsius.

Embodiment 10 is a monomer of Formula II:

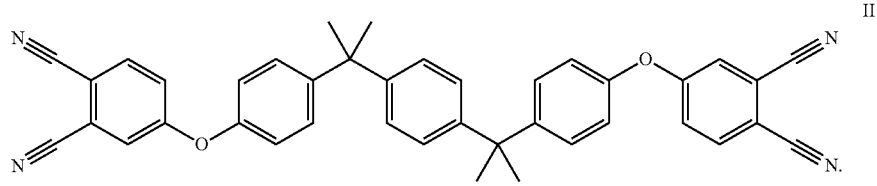 [SMILES: CC(C)(c1ccc(Oc2ccc(C#N)c(C#N)c2)cc1)c1ccc(C(C)(C)c2ccc(Oc3ccc(C#N)c(C#N)c3)cc2)cc1]

Embodiment 11 is a composition including a primary amine curative and a monomer of Formula II.

Embodiment 12 is the composition of embodiment 11, further including at least one filler.

Embodiment 13 is the composition of embodiment 11 or embodiment 12, wherein the primary amine curative comprises an aniline functional residue.

Embodiment 14 is the composition of any of embodiments 11 to 13, wherein the primary amine curative is selected from 4,4'-(1,3-phenylenedioxy)dianiline, 4,4'-(1,4-phenylenedioxy)dianiline, bis[4-(4-aminophenoxy)phenyl]sulfone, 4,4'-(4,4'-isopropylidenediphenyl-1,1'-diyldioxy)dianiline, 4,4'-(1,3-phenylenediisopropylidene)dianiline, 4,4'-(1,4-phenylenediisopropylidene)dianiline, 4,4'-(1,1'-biphenyl-4,4'-diyldioxy)dianiline, 4,4'-methylenedianiline, 4,4'-sulphonyldianiline, 4,4'-methylene-bis(2-methylaniline), 3,3'-methylenedianiline, 3,4'-methylenedianiline, 4,4'-oxydianiline, 4,4'-(isopropylidene)dianiline, 4,4'-(hexafluoroisopropylidene)dianiline, 4,4'-(hexafluoroisopropylidene)bis(p-phenyleneoxy)dianiline, 4,4'-diaminobenzophenone, and combinations thereof.

Embodiment 15 is the composition of any of embodiments 11 to 14, wherein the primary amine curative is present in an amount of between 0 and 40 percent by weight of the polymerized product.

Embodiment 16 is the polymerized product of the monomer of Formula II.

Embodiment 17 is the polymerized product of the composition of any of embodiments 11 to 16.

Embodiment 18 is the polymerized product of embodiment 17, wherein the product exhibits a glass transition temperature of 250 to 300 degrees Celsius.

Embodiment 19 is a method of making a polymerized network. The method includes obtaining a monomer of Formula I or Formula II; blending the monomer with a curative, a catalyst, or a combination thereof to form a monomer blend; and subjecting the monomer blend to a temperature of no more than 300 degrees Celsius to form a fully polymerized network. Any optional postcuring of the polymerized network consists of subjecting the polymerized network to a temperature of no more than 300 degrees Celsius.

Embodiment 20 is the method of embodiment 19, wherein the monomer is of Formula I and the monomer blend is subjected to a temperature of no more than 250 degrees Celsius.

Embodiment 21 is the method of embodiment 19, wherein the monomer is of Formula II.

Embodiment 22 is the method of any of embodiments 19 to 21, wherein the monomer blend is subjected to a temperature of no more than 300 degrees Celsius in air.

Embodiment 23 is the method of any of embodiments 19 to 22, wherein the monomer blend is subjected to a temperature of no more than 300 degrees Celsius at ambient pressure.

Embodiment 24 is a two component system including a first component including a monomer of Formula I or Formula II; and a second component including a curative.

Embodiment 25 is the two component system of embodiment 24, wherein the first component, the second component, or both, further includes at least one additive.

Embodiment 26 is the two component system of embodiment 25, wherein the at least one additive is independently selected from a toughener, a filler, or a combination thereof.

Embodiment 27 is a resin blend including a blend of at least two monomers selected from the monomers of Formula I, Formula II, and Formula III:

Embodiment 35 is the resin blend of any of embodiments 27 to 34, further including at least one additive.

Embodiment 36 is the resin blend of embodiment 35, wherein the at least one additive is selected from a catalyst, a curative, a toughener, a filler, and combinations thereof.

Embodiment 37 is the resin blend of embodiment 36, wherein the curative comprises a primary amine.

Embodiment 38 is the resin blend of embodiment 36 or embodiment 37, wherein the curative comprises an aniline functional residue.

Embodiment 39 is the resin blend of any of embodiments 36 to 38, wherein the curative is present in an amount of between 0 and 40 percent by weight of the resin blend.

Embodiment 40 is the resin blend of any of embodiment 36 to 39, wherein the at least one additive includes a toughener.

Embodiment 41 is the resin blend of any of embodiments 36 to 40, wherein the at least one additive includes a filler.

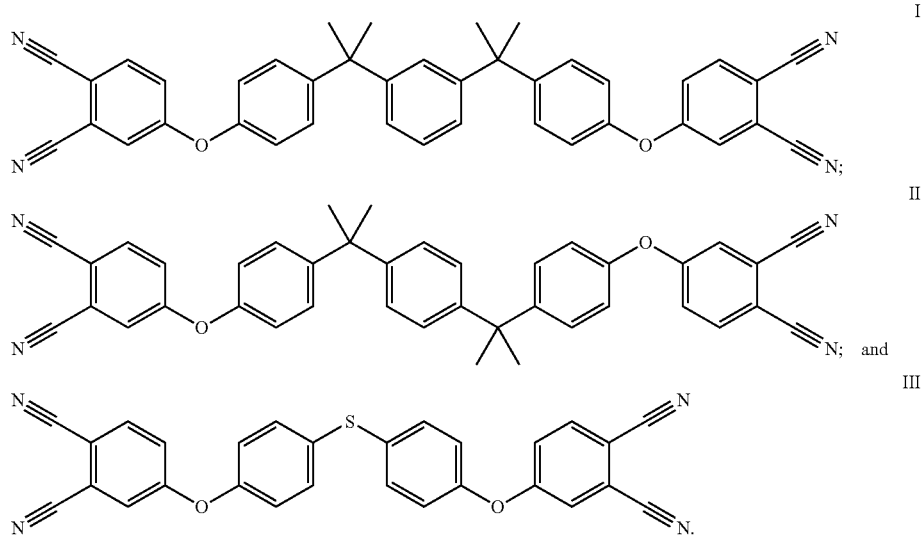

Embodiment 28 is the resin blend of embodiment 27, including a blend of the monomer of Formula I and the monomer of Formula II.

Embodiment 29 is the resin blend of embodiment 28, wherein a weight ratio of the monomer of Formula I to the monomer of Formula II ranges from 10:90 to 90:10, inclusive.

Embodiment 30 is the resin blend of embodiment 27, including a blend of the monomer of Formula I and the monomer of Formula III.

Embodiment 31 is the resin blend of embodiment 30, wherein a weight ratio of the monomer of Formula I to the monomer of Formula III ranges from 10:90 to 90:10, inclusive.

Embodiment 32 is the resin blend of embodiment 27, including a blend of the monomer of Formula II and the monomer of Formula III.

Embodiment 33 is the resin blend of embodiment 32, wherein a weight ratio of the monomer of Formula II to the monomer of Formula III ranges from 10:90 to 90:10, inclusive.

Embodiment 34 is the resin blend of embodiment 27, including a blend of the monomers of Formula I, Formula II, and Formula III.

EXAMPLES

Objects and advantages of this invention are further illustrated by the following examples, but the particular materials and amounts thereof recited in these examples, as well as other conditions and details, should not be construed to unduly limit this invention. These examples are for illustrative purposes only and are not meant to be limiting on the scope of the appended claims. Unless otherwise noted, all chemicals used in the examples can be obtained from Sigma-Aldrich Corp. (Saint Louis, Mo.)

Materials

| Name | Description |
|---|---|
| 4-nitrophthalonitrile | 4-nitrophthalonitrile (>98%) from TCI America (Portland, OR). |
| bisphenol M | bisphenol M, 4,4'-(1,3-phenylenediisopropylidene)bisphenol (>98%), from TCI America (Portland, OR). |
| bisphenol P | bisphenol P, 4,4'-(1,4-phenylenediisopropylidene)bisphenol (>98%), from TCI America (Portland, OR). |
| potassium carbonate | anhydrous potassium carbonate ($K_2CO_3$, 99%) from Alfa Aesar (Ward Hill, MA). |

-continued

| Name | Description |
|---|---|
| dimethylsulfoxide | anhydrous dimethylsulfoxide (DMSO, >99.8%) from Alfa Aesar (Ward Hill, MA). |
| methanol | ACS grade methanol from VWR (Radnor, PA). |

Methods:

Method of Measuring Cure Reaction Exotherm Via Differential Scanning Calorimeter (DSC)

A TA Instruments Q Series DSC (obtained from TA Instruments, New Castle, Del.) was used to measure the dynamic heat flow of a material under application of a constant thermal ramp rate. Approximately 5 mg of resin was weighed into an aluminum DSC pan. The sample pan was loaded into the DSC instrument, and the heat flow of the sample was measured in a dynamic DSC measurement with a thermal ramp rate of 10 degrees Celsius per minute (° C./min).

Method of Measuring the Dynamic Moduli and the Glass to Rubber Transition Temperature Via a Dynamic Mechanical Analyzer (DMA):

A TA Instruments Q Series DMA (obtained from TA Instruments, New Castle, Del.) was used to measure low strain linear viscoelastic properties. Dynamic mechanical measurements were performed using single cantilever beam geometry. The low strain in-phase and out-of-phase deformation response was measured when applying a continuous oscillatory force with a controlled deformation amplitude of 20 micrometers at a frequency of 1 Hz, and the resulting storage and loss moduli and loss tangent were calculated ramping the temperature during the measurement. The temperature was ramped at 3° C./min over a temperature range spanning the glass to rubber transition. The glass transition temperature is characterized by the storage modulus (E') onset temperature, the loss modulus (E") peak temperature, and the loss tangent (tan δ) peak temperature.

Method of Measuring Weight Loss Via Thermogravimetric Analysis (TGA)

A TA Instruments Q Series TGA (obtained from TA Instruments, New Castle, Del.) was used to measure the dynamic weight loss of a material under application of a constant thermal ramp rate. Samples of approximately 5 mg were loaded on platinum pans into the TGA. The mass loss of the sample was measured under an air atmosphere and under a nitrogen atmosphere with a thermal ramp of 10° C./min.

Method of Measuring the Complex Shear Viscosity

A TA instruments Discovery Series HR-2 stress controlled rheometer with parallel plate geometry (obtained from TA Instruments, New Castle, Del.) was used to measure the complex shear viscosity. The tooling utilized an upper 40 mm top plate and a lower temperature controlled peltier plate. The gap between the upper and lower plate was 0.5 mm. The viscosity was measured by applying a 1% strain oscillation at a frequency of 1 Hz for 6 seconds, broken into a 3 second conditioning step and a 3 second measurement step.

Method of Measuring Fourier Transform Infrared (FTIR) Absorbance Spectroscopy

A Thermo Scientific Nicolet 6700 FTIR spectrometer with Smart iTR accessory (Obtained from Thermo Fisher Scientific, Waltham, Mass.) was used to measure infrared absorbance by attenuated total reflectance (ATR). The strong spectral absorbance features that define the product are reported in $cm^{-1}$.

Method of Measuring Nuclear Magnetic Resonance (NMR) Spectroscopy

A Bruker Ultrashield 500 plus NMR spectrometer (obtained from Bruker BioSpin Corporation, Billerica, Mass.) was used to measure the proton and carbon chemical shifts. The proton and carbon chemical shifts are listed referenced to TMS. Integration of the proton resonance frequency absorption defined the number of protons observed. Proton and carbon chemical shifts and integration of the proton peaks were used to identify the material product.

Example 1

Preparation of BMPN Monomer and its Characterization.

Bisphenol M diphthalonitrile (i.e., bis(3,4-dicyanophenyl) ether of bisphenol M) was derived from the nucleophilic substitution reaction of 4-nitrophthalonitrile and bisphenol M (i.e. 4,4'-(1,3 phenylenediisopropylidene) bisphenol). To a three necked 500 mL reaction flask was added 18 g (0.104 mol) of 4-nitrophthalonitrile, 18.02 g (0.052 mol) of bisphenol M, 28.74 g (0.208 mol) of anhydrous $K_2CO_3$ and 180 g of dry DMSO), then stirred for 48 hours at room temperature under a nitrogen atmosphere. The reaction solution was poured into 600 mL of stirring deionized water, leaving undissolved salts behind in the reaction flask. The precipitated product was collected on a Buchner funnel by suction filtration. The precipitate was added to 200 mL of methanol and stirred for 30 minutes to remove impurities. The solid product was collected a second time on a Buchner funnel by suction filtration and washed with 200 ml of methanol. The product was collected and dried in a convection oven at 120° C. The product, 28.42 g (91.3%), had a melt temperature of 160° C. as measured by differential scanning calorimetry, and was identified as the desired compound by infrared and NMR analysis.

The BMPN was tested for its ability to exist as a supercooled liquid through monitoring the resin viscosity at a temperature, 135° C., below the resin melt temperature. The viscosity was periodically measured according to the Method of Measuring the Complex Shear Viscosity, by applying a 1% strain oscillation at a frequency of 1 Hz for 6 seconds using the parallel plate geometry with a gap of 0.5 mm. The still time between measurements was varied to study the impact of the periodic measurement cycle on cold crystallization (i.e., crystallization of the resin below the resin melt temperature). Results are listed in Table 1 below. When sampling the viscosity every 10 minutes with a 6 second measurement period, the BMPN remained in a supercooled liquid state for more than 3 days with no sign of crystallization. When the sampling time was changed to 30 minutes and 60 minutes, the BMPN showed evidenced of cold crystallization by an increase in the resin viscosity after 7.5 hours and 4 hours, respectively. Small crystallites formed; however the majority of the sample remained liquid for several hours after the increase in viscosity, signaling crystallite formation when the measurement was terminated.

BMPN characterizing data: DSC $T_m$=160° C. FTIR (ATR; $cm^{-1}$): 2231 (—CN), 1247 (C—O—C). $^1$H NMR (500 MHz, $CDCl_3$ with 0.05% v/v TMS; δ, ppm): 7.72 (d, J=8.60 Hz, 2H), 7.28 (d, J=8.75 Hz, 4H), 7.24 (d, J=2.46 Hz, 2H), 7.23 (t, J=2.55, 1H), 7.22 (d, J=2.38 Hz, 2H), 7.11 (s, 2H), 7.09 (d, J=1.73, 1H), 6.95 (d, J=8.74, 4H), 1.68 (s, 12H). $^{13}$C NMR (500 MHz, $CDCl_3$ with 0.05% v/v TMS; δ, ppm):

161.93, 151.12, 149.70, 149.08, 135.38, 128.99, 127.90, 125.23, 124.33, 121.44, 121.12, 120.00, 117.51, 115.44, 115.04, 108.57, 42.93, 30.83.

TABLE 1

Viscosity monitoring of resin crystallization

| Resin | Temperature [° C.] | Sampling interval [min] | Time [hr] | Crystals |
|---|---|---|---|---|
| BMPN | 135 | 10 | 72 | no |
| BMPN | 135 | 30 | 7.5 | yes |
| BMPN | 135 | 60 | 4 | yes |

Example 2

Preparation of BPPN Monomer and its Characterization.

Bisphenol P diphthalonitrile (i.e., bis(3,4-dicyanophenyl) ether of bisphenol P) was derived from the nucleophilic substitution reaction of 4-nitrophthalonitrile and bisphenol P (i.e. 4,4'-(1,4-phenylenediisopropylidene)bisphenol). To a three necked 250 mL reaction flask was added 9.1 g (0.052 mol) of 4-nitrophthalonitrile, 9.11 g (0.026 mol) of bisphenol M, 14.53 g (0.105 mol) of anhydrous $K_2CO_3$ and 90 g of dry DMSO), then stirred for 48 hours at room temperature under a nitrogen atmosphere. The reaction solution was poured into 300 mL of stirring deionized water, leaving undissolved salts behind in the reaction flask. The precipitated product was collected on a Buchner funnel by suction filtration. The precipitate was added to 100 mL of methanol and stirred for 30 minutes to remove impurities. The solid product was collected a second time on a Buchner funnel by suction filtration and washed with 100 ml of methanol. The product was collected and dried in a convection oven at 120° C. The product, 13.2 g (83.9%), had a melt temperature of 210° C. as measured by differential scanning calorimetry. The product was identified as the desired compound by infrared and NMR analysis.

BPPN characterizing data: DSC $T_m$=213° C. FTIR (ATR; $cm^{-1}$): 2229 (—CN), 1249 (C—O—C). $^1H$ NMR (500 MHz, $CDCl_3$ with 0.05% v/v TMS; δ, ppm): 7.72 (d, J=9.38 Hz, 2H), 7.33 (d, J=8.78 Hz, 4H), 7.26 (d, J=3.38 Hz, 4H), 7.17 (s, 4H), 6.97 (d, J=8.77 Hz, 4H), 1.71 (s, 12H). $^{13}C$ NMR (500 MHz, $CDCl_3$ with 0.05% v/v TMS; δ, ppm): 161.90, 151.20, 149.00, 147.40, 135.35, 129.04, 126.43, 121.52, 121.21, 120.01, 117.53, 115.43, 115.06, 108.62, 42.44, 30.86.

Comparative Example 1

Preparation of RPN Monomer and its Characterization.

Resorcinol diphthalonitrile (i.e., bis(3,4-dicyanophenyl) ether of resorcinol) was derived from the nucleophilic substitution reaction of 4-nitrophthalonitrile and resorcinol. To a three necked 500 mL reaction flask was added 18 g (0.104 mol) of 4-nitrophthalonitrile, 5.72 g (0.52 mol) of resorcinol, 28.74 g (0.208 mol) of anhydrous $K_2CO_3$ and 180 g of dry DMSO), then stirred for 48 hours at room temperature under a nitrogen atmosphere. The reaction solution was poured into 600 mL of stirring deionized water, leaving undissolved salts behind in the reaction flask. The precipitated product was collected on a Buchner funnel by suction filtration. The precipitate was added to 200 mL of methanol and stirred for 30 minutes to remove impurities. The solid product was collected a second time on a Buchner funnel by suction filtration and washed with 200 mL of methanol. The product was collected and dried in a convection oven at 120° C. The product, 17 g (90.3%), had a melt temperature of 185° C. The product was identified as the desired compound by infrared and NMR analysis.

RPN characterizing data: DSC $T_m$=185° C. FTIR (ATR; $cm^{-1}$): 2231 (—CN), 1244 (C—O—C). $^1H$ NMR (500 MHz, $CDCl_3$ with 0.05% v/v TMS; δ, ppm): 7.79 (d, J=8.68 Hz, 2H), 7.57 (t, J=8.24 Hz, 1H), 7.37 (d, J=2.52 Hz, 2H), 7.33 (q, $J_{ab}$=8.68 Hz, $J_{bc}$=20.54, 2H), 7.03 (q, $J_{ab}$=8.25 Hz, $J_{bc}$=2.30, 2H), 6.86 (t, J=2.27 Hz, 1H), $^{13}C$ NMR (500 MHz, $CDCl_3$ with 0.05% v/v TMS; δ, ppm): 160.68, 155.46, 135.66, 132.35, 122.05, 122.01, 117.86, 117.71, 115.15, 114.78, 112.88, 109.83.

Example 3

Polymerization of the Phthalonitrile Monomer of Example 1 with 4,4'-(1,3-Phenyleneoxy)Aniline Curative.

8.0 g of BMPN was melt blended at a temperature of 190° C. in a flat bottom 70 mm diameter thin gauge aluminum pan. 4,4'-(1,3-phenyleneoxy)aniline was added to the resin blend at 4 pph by mass and stirred into the resin at 190° C. The resin was placed in an air circulating oven and cured for 15 hours at 200° C. and 5 hours at 250° C., ramping 3° C./min between set points. The resin underwent a thermosetting network polymerization to a hard stiff solid. The solid sample was cooled at 5° C./min to 40° C. and removed from the aluminum pan. The sample was cut into strips for DMA measurement of the stiffness (E') and glass transition temperature (tan δ peak) in single cantilever beam geometry. A DMA specimen was subjected to a thermal heating ramp up to 350° C. at 3° C./min. The specimen was further post cured for 5 hours at 300° C. and 2 hours at 350° C. under an inert nitrogen atmosphere, and subjected to a second DMA measurement up to 350° C., monitoring for a change in the specimen mechanical response due to residual cure. No change was witnessed in the mechanical response. Thermal degradation resistance was evaluated by thermal gravimetric analysis of two 5 mg specimens under air and nitrogen with a heating ramp rate of 10° C./min.

Example 4

Polymerization of the Phthalonitrile Monomer of Example 2 with 4,4'-(1,3-Phenyleneoxy)Aniline Curative.

8.0 g of BPPN was melt blended at a temperature of 230° C. in a flat bottom 70 mm diameter thin gauge aluminum pan. 4,4'-(1,3-phenyleneoxy)aniline was added to the resin blend at 4 pph by mass and stirred into the resin at 230° C. The resin was placed in an air circulating oven and cured for 2 hours at 230° C. and 5 hours at 300° C., ramping 3° C./min between set points. The resin underwent a thermosetting network polymerization to a hard stiff solid. The solid sample was cooled at 5° C./min to 40° C. and removed from the aluminum pan. The sample was cut into strips for DMA measurement of the stiffness (E') and glass transition temperature (tan δ peak) in single cantilever beam geometry. A DMA specimen was subjected to a thermal heating ramp up to 350° C. at 3° C./min. The specimen was further post cured for 1 hour at 375° C. under an inert nitrogen atmosphere, and subjected to a second DMA measurement up to 350° C., monitoring for a change in the specimen mechanical response due to residual cure. No change was witnessed in the mechanical response. Thermal degradation resistance was evaluated by thermal gravimetric analysis of two 5 mg specimens under air and nitrogen with a heating ramp rate of 10° C./min.

Comparative Example 2

Polymerization of the Phthalonitrile Monomer of Comparative Example 1 with 4,4'-(1,3-Phenyleneoxy)Aniline Curative.

8.0 g of RPN was melt blended at a temperature of 190° C. in a flat bottom 70 mm diameter thin gauge aluminum pan. 4,4'-(1,3-phenyleneoxy)aniline was added to the resin blend at 4 pph by mass and stirred into the resin at 190° C. The resin was placed in an air circulating oven and cured for 2 hours at 230° C. and 5 hours at 300° C., ramping 3° C./min between set points. The resin underwent a thermosetting network polymerization to a hard stiff solid. The solid sample was cooled at 5° C./min to 40° C. and removed from the aluminum pan. The sample was further post cured at 350° C. for 1 hour, 375° C. for 1 hour, 400° C. for 30 minutes, and 450° C. under a flow of nitrogen in a tube furnace ramping 3° C./min between set points, and then cooled at 5° C./min to 40° C. The sample was cut into strips for DMA measurement of the stiffness (E') and glass transition temperature (tan δ peak) in single cantilever beam geometry. A DMA specimen was subjected to two thermal heating ramps up to 450° C. at 3° C./min monitoring for residual cure at higher temperatures. Thermal degradation resistance was evaluated by thermal gravimetric analysis of two 5 mg specimens under air and nitrogen with a heating ramp rate of 10° C./min.

to 0° C. at 3° C./min and a second heating ramp to 350° C. at 3° C./min, monitoring for a change in the specimen mechanical response between the first and second heating ramps as evidence of residual cure. No change was witnessed in the mechanical response. Thermal degradation resistance was evaluated by thermal gravimetric analysis of two 5 mg specimens under air and nitrogen with a heating ramp rate of 10° C./min.

Example 6

Polymerization of the Phthalonitrile Monomer of Example 1 with 4,4'-Sulphonyldianiline Curative.

8.0 g of BMPN was melt blended at a temperature of 190° C. in a flat bottom 70 mm diameter thin gauge aluminum pan. 4,4'-sulphonyldianiline was added to the resin blend at 3.4 pph by mass and stirred into the resin at 190° C. The resin was placed in an air circulating oven and cured for 15 hours at 200° C., 5 hours at 250° C. and 12 hours at 285° C., ramping 3° C./min between set points. The resin underwent a thermosetting network polymerization to a hard stiff solid. The solid sample was cooled at 5° C./min to 40° C. and removed from the aluminum pan. The sample was cut into strips for DMA measurement of the stiffness (E') and glass transition temperature (tan δ peak) in single cantilever beam geometry. A DMA specimen was subjected to a thermal heating ramp up to 350° C. at 3° C./min, followed by cooling to 0° C. at 3° C./min and a second heating ramp to 350° C. at 3° C./min monitoring for a change in the specimen mechanical response between the first and second heating ramps as evidence of residual cure. No change was wit-

TABLE 2

DMA mechanical properties

| | | | DMA (single cantilever, 3° C./min ramp) | | | | TGA (10° C./min ramp) | |
|---|---|---|---|---|---|---|---|---|
| Cured PN Network | | | E' (25° C.) | Tg (E' onset) | Tg (E" peak) | Tg (tan d peak) | 5% wt loss | |
| Example | Resin | Curative | [MPa] | [° C.] | [° C.] | [° C.] | Air [° C.] | $N_2$ [° C.] |
| Ex 3 | BMPN | 4,4'-(1,3-phenyleneoxy)aniline | 2840 | 209 | 213 | 229 | 489 | 478 |
| Ex 4 | BPPN | 4,4'-(1,3-phenyleneoxy)aniline | 2560 | 264 | 268 | 287 | 489 | 477 |
| CE 2 | RPN | 4,4'-(1,3-phenyleneoxy)aniline | 3560 | 412 | >450 | >450 | 507 | 497 |

Example 5

Polymerization of the Phthalonitrile Monomer of Example 1 with 4,4'-Methylenedianiline Curative.

8.0 g of BMPN was melt blended at a temperature of 190° C. in a flat bottom 70 mm diameter thin gauge aluminum pan. 4,4'-methylenedianiline was added to the resin blend at 2.8 pph by mass and stirred into the resin at 190° C. The resin was placed in an air circulating oven and cured for 15 hours at 200° C., 5 hours at 250° C. and 12 hours at 285° C., ramping 3° C./min between set points. The resin underwent a thermosetting network polymerization to a hard stiff solid. The solid sample was cooled at 5° C./min to 40° C. and removed from the aluminum pan. The sample was cut into strips for DMA measurement of the stiffness (E') and glass transition temperature (tan δ peak) in single cantilever beam geometry. A DMA specimen was subjected to a thermal heating ramp up to 350° C. at 3° C./min, followed by cooling nessed in the mechanical response. Thermal degradation resistance was evaluated by thermal gravimetric analysis of two 5 mg specimens under air and nitrogen with a heating ramp rate of 10° C./min.

Example 7

Polymerization of the Phthalonitrile Monomer of Example 1 with 4,4'-(4,4'-Isopropylidenediphenyl-1,1'-Diyldioxy)Dianiline Curative.

8.0 g of BMPN was melt blended at a temperature of 190° C. in a flat bottom 70 mm diameter thin gauge aluminum pan. 4,4'-(4,4'-Isopropylidenediphenyl-1,1'-diyldioxy)dianiline was added to the resin blend at 5.5 pph by mass and stirred into the resin at 190° C. The resin was placed in an air circulating oven and cured for 15 hours at 200° C. and 5 hours at 250° C., ramping 3° C./min between set points. The resin underwent a thermosetting network polymerization to a hard stiff solid. The solid sample was cooled at 5° C./min to 40° C. and removed from the aluminum pan. The sample was cut into strips for DMA measurement of the stiffness (E') and glass transition temperature (tan δ peak) in single cantilever beam geometry. A DMA specimen was subjected to a thermal heating ramp up to 350° C. at 3° C./min. The specimen was further post cured for 5 hours at 300° C. and 2 hours at 350° C. under an inert nitrogen atmosphere, and subjected to a second DMA measurement up to 350° C. monitoring for a change in the specimen mechanical response due to residual cure. No change was witnessed in the mechanical response. Thermal degradation resistance was evaluated by thermal gravimetric analysis of two 5 mg specimens under air and nitrogen with a heating ramp rate of 10° C./min.

TABLE 3

| | | | DMA mechanical properties | | | | | |
|---|---|---|---|---|---|---|---|---|
| | | | | DMA (single cantilever, 3° C./min ramp) | | | TGA (10° C./min ramp) | |
| Cured PN Network | | | E' (25° C.) | Tg (E' onset) | Tg (E" peak) | Tg (tan d peak) | 5% wt loss | |
| Example | Resin | Curative | [MPa] | [° C.] | [° C.] | [° C.] | Air [° C.] | N₂ [° C.] |
| Ex 3 | BMPN | 4,4'-(1,3-phenyleneoxy)aniline | 2840 | 209 | 213 | 229 | 489 | 478 |
| Ex 5 | BMPN | 4,4'-methylenedianiline | 2945 | 205 | 209 | 245 | 484 | 482 |
| Ex 6 | BMPN | 4,4'-sulphonyldianiline | 2830 | 217 | 222 | 236 | 485 | 484 |
| Ex 7 | BMPN | 4,4'-(4,4'-Isopropylidene diphenyl-1,1'-diyldioxy)dianiline | 2935 | 210 | 212 | 230 | 489 | 483 |

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A monomer of Formula I:

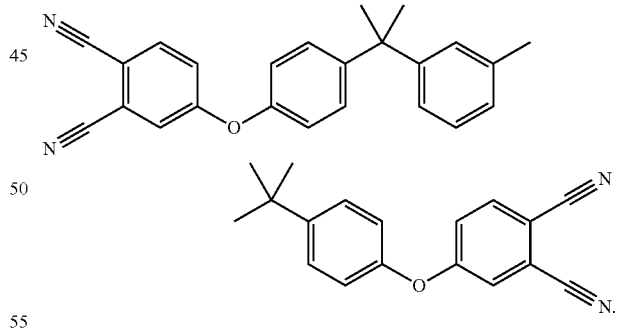

2. A composition comprising a primary amine curative and a monomer of Formula I:

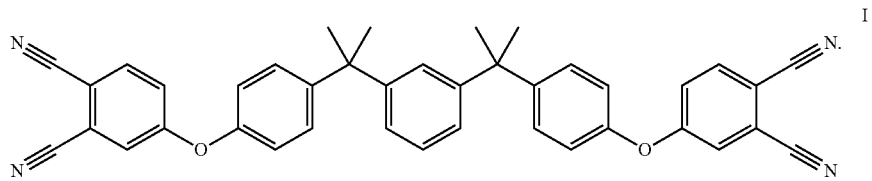 [SMILES: CC(C)(c1ccc(Oc2ccc(C#N)c(C#N)c2)cc1)c1cccc(C(C)(C)c2ccc(Oc3ccc(C#N)c(C#N)c3)cc2)c1]

3. The composition of claim 2, wherein the primary amine curative comprises an aniline functional residue.

4. The polymerized product of the composition of claim 2.

5. The polymerized product of the monomer of Formula I:

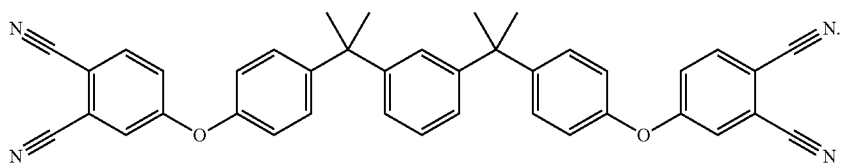 [SMILES: CC(C)(c1ccc(Oc2ccc(C#N)c(C#N)c2)cc1)c1cccc(C(C)(C)c2ccc(Oc3ccc(C#N)c(C#N)c3)cc2)c1]

I

6. A composition comprising a primary amine curative and a monomer of Formula II:

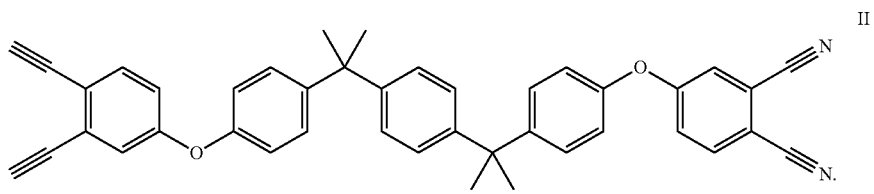 [SMILES: C#Cc1ccc(Oc2ccc(C(C)(C)c3ccc(C(C)(C)c4ccc(Oc5ccc(C#N)c(C#N)c5)cc4)cc3)cc2)cc1C#C]

II

7. The composition of claim 6, wherein the primary amine curative comprises an aniline functional residue.

8. The polymerized product of the composition of claim 6.

9. The polymerized product of the monomer of Formula II:

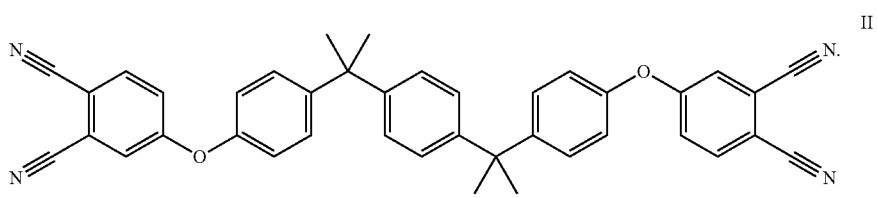 [SMILES: CC(C)(c1ccc(Oc2ccc(C#N)c(C#N)c2)cc1)c1ccc(C(C)(C)c2ccc(Oc3ccc(C#N)c(C#N)c3)cc2)cc1]

II

10. A method of making a polymerized network, the method comprising:
obtaining a monomer of Formula I or Formula II:

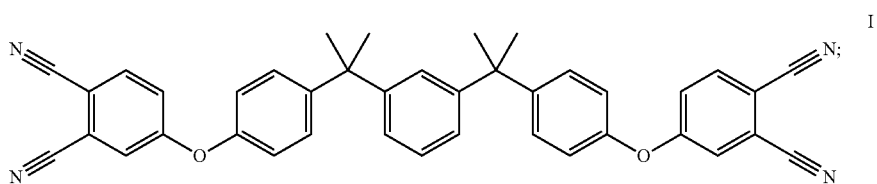

I

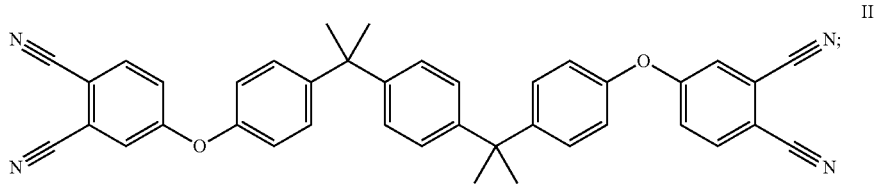

II blending the monomer with a curative, a catalyst, or a combination thereof to form a monomer blend; and subjecting the monomer blend to a temperature of no more than 300 degrees Celsius to form a fully polymerized network, wherein any optional postcuring of the polymerized network consists of subjecting the polymerized network to a temperature of no more than 300 degrees Celsius.

11. A two component system comprising:

a first component comprising a monomer of Formula I or Formula II:

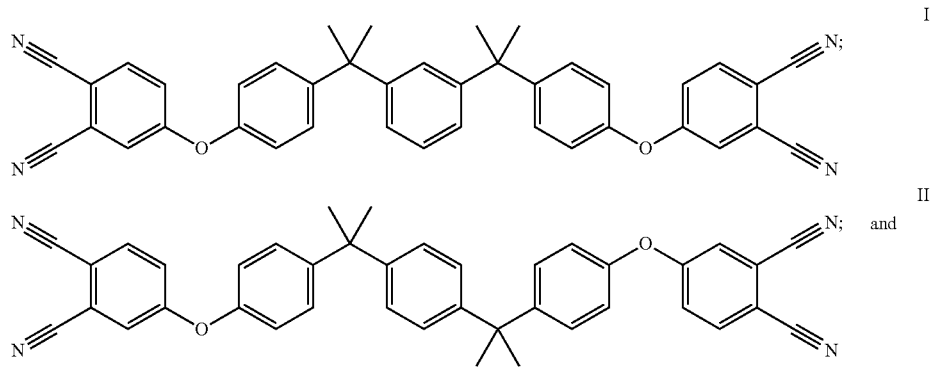

a second component comprising a curative.

12. A resin blend comprising a blend of at least two monomers selected from the monomers of Formula I, Formula II, or Formula III:

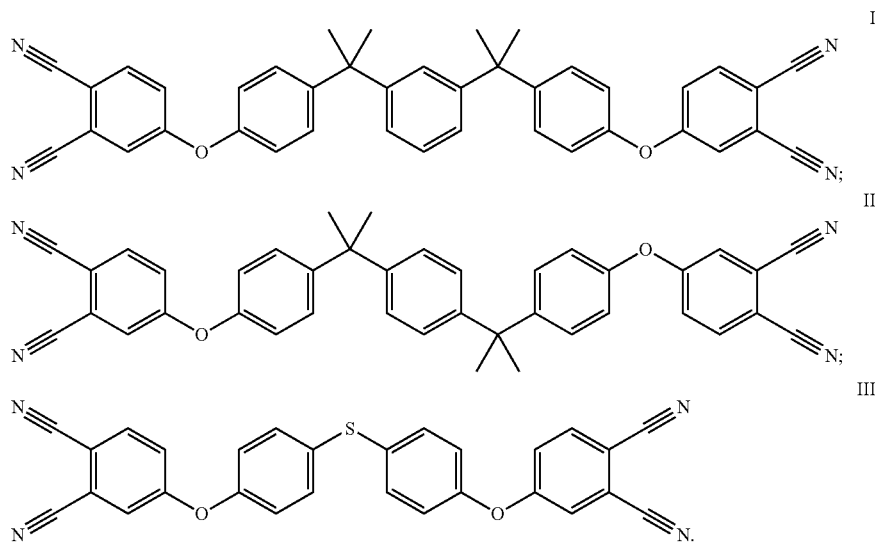

* * * * *

UNITED STATES PATENT AND TRADEMARK OFFICE
CERTIFICATE OF CORRECTION

PATENT NO. : 11,401,364 B2  
APPLICATION NO. : 16/078073  
DATED : August 2, 2022  
INVENTOR(S) : Benjamin John Anderson It is certified that error appears in the above-identified patent and that said Letters Patent is hereby corrected as shown below:

In the Claims

Column 28  
Line 42, In Claim 1, delete:  
"1. A monomer of Formula I:

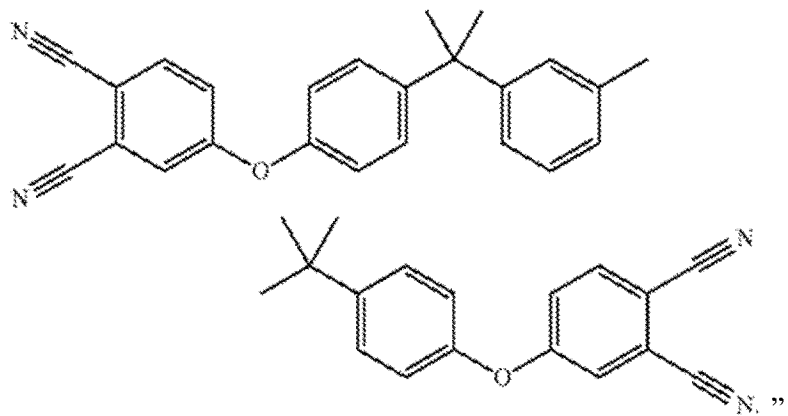

And insert:  
-- 1. A monomer of Formula I:

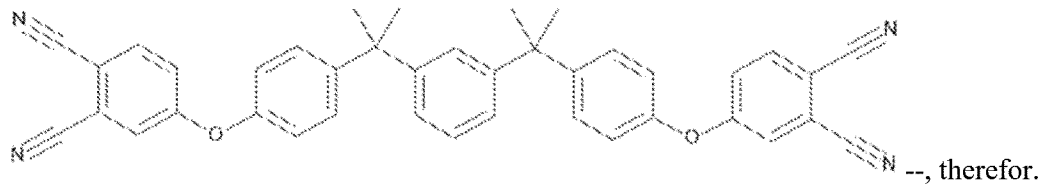

--, therefor.

Column 29  
Line 7 (approx.), In Claim 5, insert -- I -- after

Signed and Sealed this  
Twenty-eighth Day of February, 2023

Katherine Kelly Vidal  
*Director of the United States Patent and Trademark Office*

CERTIFICATE OF CORRECTION (continued)
U.S. Pat. No. 11,401,364 B2

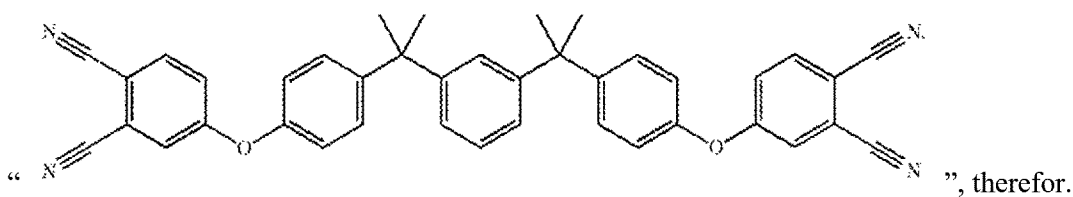
" ", therefor.

Column 29
Line 18 (approx.), In Claim 6, delete:

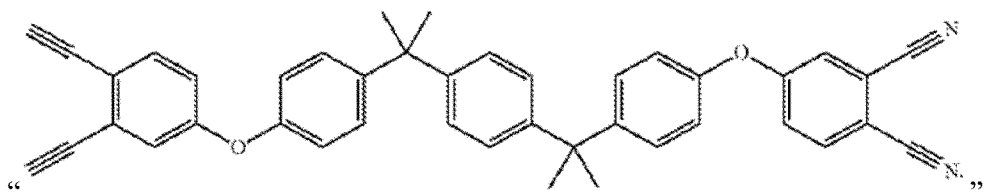
" "

And insert:

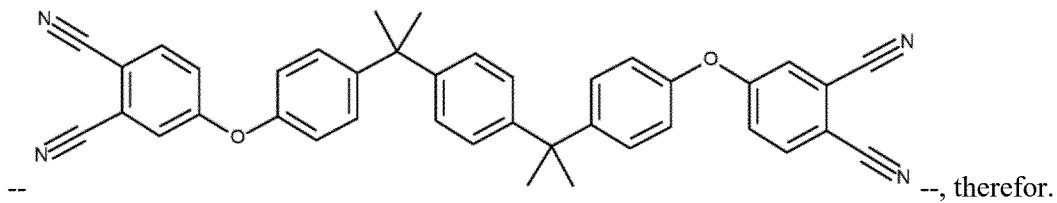
-- --, therefor.